US00PP09315P

United States Patent [19]

Zerr

[11] Patent Number: Plant 9,315

[45] Date of Patent: Oct. 3, 1995

[54] POINSETTIA PLANT NAMED 'FISPUE'

[75] Inventor: Katharina Zerr, Simmern, Germany

[73] Assignee: Florfis, AG, Binningen, Switzerland

[21] Appl. No.: 328,052

[22] Filed: Oct. 24, 1994

[30] Foreign Application Priority Data

Dec. 29, 1993 [DE] Germany ..... EUP 149

[51] Int. Cl.[6] ..... A01H 5/00

[52] U.S. Cl. ..... Plt./86.1

[58] Field of Search ..... Plt./86.1, 86.4

[56] References Cited

U.S. PATENT DOCUMENTS

P.P. 8,259 6/1993 Jacobsen ..... Plt./86.4

*Primary Examiner*—James R. Feyrer

*Attorney, Agent, or Firm*—Foley & Lardner

[57] ABSTRACT

A distinct cultivar of poinsettia plant named Fispue, characterized by the combined traits of light pink bracts with white margin, medium tall and well branched plant habit, medium green foliage, medium early flowering response, and early coloring of the bracts in relation to the maturing of the bracts.

2 Drawing Sheets

Fispue is a product of a mutation induction program carried out by the inventor in Hillscheid, Germany in 1991. The primary objective of the induction program was to expand the bract color ranges of Peterstar, disclosed in U.S. Plant Pat. No. 8,259 and characterized by its bright red bract color, medium green foliage, comparatively compact plant habit, medium early response in autumn, and good branching ability.

The irradiation program resulting in the new cultivar comprised exposing rooted cuttings taken from the plants of the parent cultivar to an X-ray source in Ahrensburg, Germany under the superivision of the inventor. The radiation dosage was 30 Gy. The irradiated plants were grown out in a greenhouse in Hillscheid, Germany and were asexually propagated by taking cuttings. These cuttings were grown outdoors near Galdar, Gran Canaria, Spain, under the supervision of the inventor. Parts of plants showing mutation were cut from the remainder of the plants by the inventor and planted as cuttings. The plants grown from these cuttings were identified by number and selections were made by the inventor in autumn 1991.

The new cultivar evolved from a flowering branch of an irrariated plant in which part of the bracts had undergone mutation and showed light pink and white coloring. The mutated plant was given the designation No. 233 and was grown out and propagated several times by cuttings by the inventor in Hillscheid, Germany in order to eliminate unstable/partial chimeras and select this specific chimera to obtain a plant with stable and uniform characteristics.

Horticultural examination initiated in 1992 and continuing thereafter has demonstrated that the combination of characteristics as here disclosed for Fispue are firmly fixed and are retained through successive generations of asexual reproduction.

The following traits have been repeatedly observed and are determined to be basic characteristics of Fispue which in combination distinguish this pointsettia as a new and distinct cultivar:

1. Light pink bracts with white margins.
2. Early coloring of the bracts in relation to the maturing of the cyathia.
3. Medium tall and well branched plant habit.
4. Medium green foliage.
5. Medium flowering response.

Fispue has not been observed under all possible environmental conditions. The phenotype may vary significantly with variations in environment such as temperature, light intensity, and daylength without, however, any variance in genotype. The following observations, measurements and comparisons describe plants grown in Hillscheid, Germany, under greenhouse conditions which approximate those generally used in commerical practice.

In comparison to the sibling cultivar Fisbala, obtained in the same mutation induction program and disclosed in a pending application, Fispue also has pink and white variegated bracts but the central pink part in the bracts of Fispue predominates and the width of the white margin is much smaller. The pink bract coloring of Fispue is less intense (RHS 51C compared to RHS 51B on mature bracts and 51A on younger bracts of Fisbala) but more uniform. However, good coloration is developed somewhat earlier in Fispue so that plants can be marketed 1–2 weeks earlier. In addition, the bracts of Fispue are larger and more elliptical and have a comparatively smooth surface.

In comparison to the commercial but unpatented cultivar Marbella, Fispue is significantly less vigorous (height 30–35 cm compared to 50 cm for Marbella). In Fispue, cyathia mature earlier and bract coloration develops faster whereby saleable plants are ready earlier. The bracts are larger than the bracts of Marbella, and have broad, rounded bases compared to the wedge-shaped bracts of Marbella. Further, the bracts of Fispue are directed more upwardly at the beginning and are imbricated to a much greater extent that the weakly rugose bracts of Marbella.

When compared to Peterstar, Fispue has light pink and white flowers, larger bracts, and a more vigorous growth habit.

The accompanying color photographic drawings show typical inflorescence and foliage of Fispue, with colors being as true as possible with illustrations of this type.

In the photograph on Sheet 1, which does not accurately depict bract color, a typical mature potted plant of Fispue appears on the left and a mature potted plant of comparison cultivar Marbella appears on the right. The photo on Sheet 2 is of a single plant of Fispue, with the bract color being accurately depicted.

In the following description, color references are made to the The Royal Horticultural Society Colour Chart. The color values were determined indoors in a north light. The plants described were grown in Hillscheid, Germany (latitude 50° N). They were planted as rooted cuttings into 14 cm pots in early August, potted in late-August and pinched 10 days later. Plants were lighted (long day conditions) from mid-September. From October 1, the plants were grown in a greenhouse natural, short day conditions at 18° C. night temperature and 18° to 24° C. day temperature. Observations and measurements were taken at the beginning of flowering when three (3) cyathias were open.

Classification:

*Botanical.—Euphorbia pulcherrima.*

*Commerical.*—Poinsettia, cv. Fispue.

Parentage: Induced mutation of Peterstar.

Plant description:

*Form.*—Medium, bushy, 8 branches.

*Growth habit.*—Medium height: 30–35 cm.

*Rooting.*—Fast, less than 20 days.

*Blooming season.*—From Dec. 1, 9 weeks of response time.

*Blooming habit.*—Saleable around December, when 3–6 bracts are fully colored.

*Foliage.*— Size: Leaf is approximately 16 cm in length; petiole is 8 cm in length. Internodes: 15–25 mm. Color: New foliage: Upper surface, between 143A and 144A; under surface 144A. Old foliage: Upper surface, medium green between 137A and 147A; under surface 137C. Leaf petiole: Light green. Shape: Large broad elliptical with very weak lobes. Texture: Upper side, weak rugosity; lower side, weak veins. Edge of margin: Entire. Disease resistance: None observed.

Flowering description:

*Cyathias.*—Borne: Initially in a narrow cluster, later growing somewhat apart. Quantity: 20–24. Retention: Good.

*Bracts.*—Elliptical shape, with broad, slightly rounded base; slightly folded, but only weakly rugose (imbricated) surface; largest colored bract with petiole is 20–21 cm long.

*Color.*—Mature leaves light pink 51C with irregularly shaped cream-white margin; new bracts are somewhat more intense in color.

*Aspect.*—Initially slightly upward, later somewhat reflexed (tips overhanging).

Reproductive organs:

*Glands, nectar cups.*—Orange-yellow.

*Stamens.*—Light brown, hardly any fertile stamens.

*Pollen.*—No pollen.

*Styles.*—Whitish, 6-lobed stigma.

*Ovaries.*—Triangular, 3-celled, 3 ovules.

I claim:

1. A new and distinct poinsettia plant named Fispue, as illustrated and described.

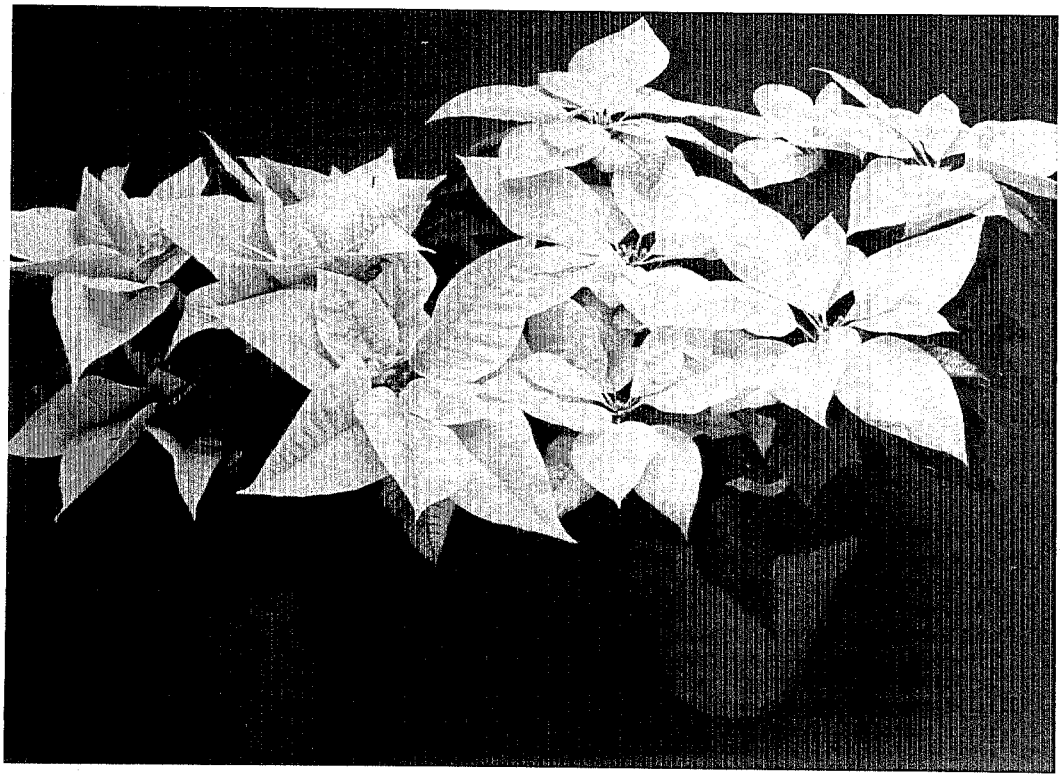

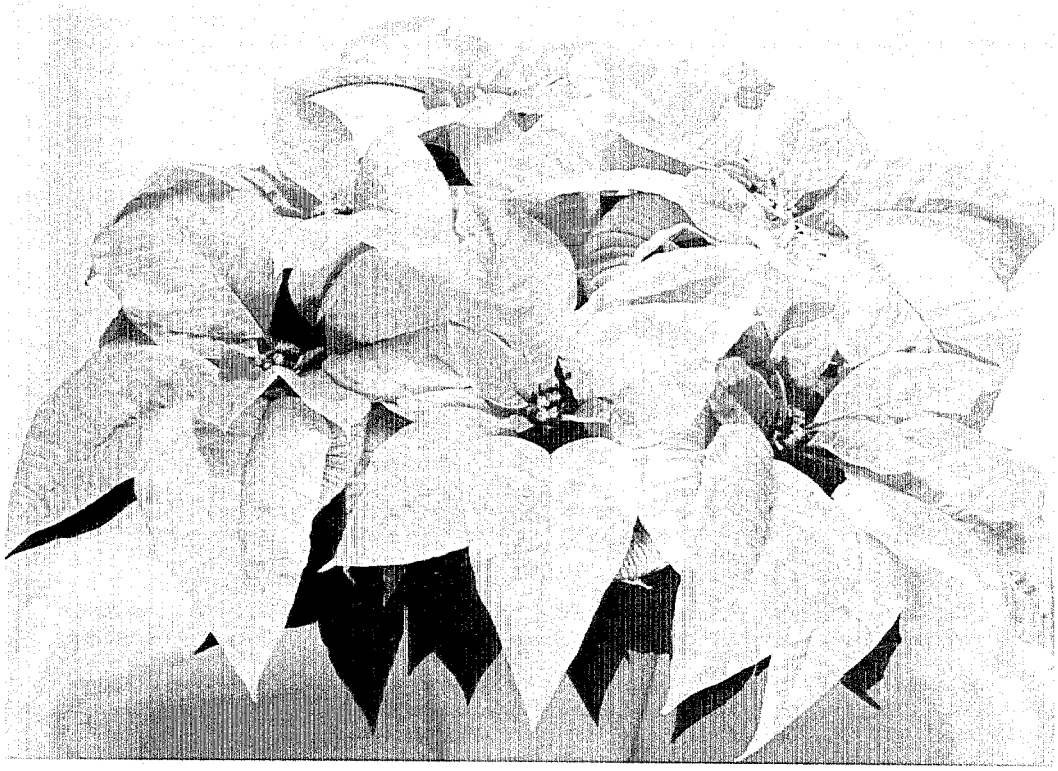

* * * * *